US00PP12207P2

(12) United States Plant Patent
Colfer

(10) Patent No.: US PP12,207 P2
(45) Date of Patent: Nov. 20, 2001

(54) ARTICHOKE PLANT NAMED 'PS-MSG0292'

(75) Inventor: William J. Colfer, Aptos, CA (US)

(73) Assignee: Seed Research Services, LLC, Salinas, CA (US)

( * ) Notice: Subject to any disclaimer, the term of this patent is extended or adjusted under 35 U.S.C. 154(b) by 0 days.

(21) Appl. No.: 09/482,606

(22) Filed: Jan. 14, 2000

(51) Int. Cl.[7] ..... A01H 5/00
(52) U.S. Cl. ..... Plt./258
(58) Field of Search ..... Plt./258

(56) References Cited

U.S. PATENT DOCUMENTS

P.P. 2,738 * 5/1967 Montgomery et al. ..... Plt./258

* cited by examiner

*Primary Examiner*—Bruce R. Campell
*Assistant Examiner*—Wendy C Baker
(74) *Attorney, Agent, or Firm*—Foley & Lardner

(57) ABSTRACT

A new and distinct cultivar of Artichoke plant named 'PS-MSG0292' characterized by having male sterility which is demonstrated by the absence of pollen on all florets during anthesis. The new cultivar has numerous, large, non-glossy heads and thick, fleshy bracts and hearts. 'PS-MSG0292' shows uniformity of head shapes and a compact, reduced plant growth habit.

3 Drawing Sheets

BACKGROUND OF THE INVENTION

The present invention comprises a new and distinct cultivar of artichoke plant, botanically known as *Cynara scolymus L.* and herein referred to by the cultivar name 'PS-MSG0292'.

*Cynara scolymus L.*, commonly known as Globe artichoke, is a thistle-like perennial herb and is a member of the family Asteraceae. Globe artichokes comprise leaves which are pinnately lobed but primarily spineless, globose capitula composed of overlapping layers of large involucral bracts, and receptacles which are enlarged and fleshy. Globe artichoke plants may be propagated by division and are essentially grown for the production of the immature flower heads, which are considered as vegetable delicacies. Fresh artichokes may be steamed or boiled, after which the fleshy receptacle, inner and outer bracts, and parts of the floral stem may be eaten.

The new cultivar is a product of a planned breeding program carried out by the inventor, William J. Colfer, at Chowchilla, Calif. in 1996. 'PS-MSG0292' was discovered and selected within the progeny of open-pollinated proprietary cultivar GGMSC6 by the inventor, William J. Colfer.

Asexual reproduction of the new cultivar by division was performed by the inventor in Watsonville, Calif. in 1997, and has demonstrated that the combination of characteristics as herein disclosed for the new cultivar are firmly fixed and retained through successive generations of asexual reproduction.

BRIEF DESCRIPTION OF THE INVENTION

The following traits have been repeatedly observed and are determined to be basic characteristics of 'PS-MSG0292' which in combination distinguish this Artichoke as a new and distinct cultivar:

1. Male sterility which is demonstrated by the absence of pollen on all florets during anthesis;

2. Numerous, large, non-glossy heads;
3. Thick, fleshy bracts and hearts;
4. Uniformity of head shapes; and,
5. Compact, reduced plant growth habit.

'PS-MSG0292' has not been observed under all possible environmental conditions. The phenotype of the new cultivar may vary with variations in environment such as temperature, humidity, light intensity and daylength, without any change in the genotype. The following observations, measurements and values describe the new cultivar as grown in Chowchilla, Calif. under conditions which closely approximate those generally used in horticultural practice.

Chowchilla is located in California's central San Juaquin valley. Conditions can vary greatly during the summer months. Air temperatures can range between the low 60's (F.) to temperatures well over 100° F. Relative humidity is generally low with values ranging from the mid 40's to the high 60's. Prevailing winds are westerly and rainfall averages rarely exceed 15" (inches) of rainfall.

In the following description, holding quality was measured by the physical appearance of the head. This includes the head's appearance following 3, 7, and 10-day storage periods in cold storage at 34° F. The head's exterior (oxidation) was observed at each of the three observation points. Browning and blackening of plant tissue was evaluated as light, moderate and extreme. Juiciness was measured by observing visible exudate and rated as absent, moderate-presence or excess. Overall storage response was measured by observing heads following 3, 7 and 10-day cold storage periods. These observations concentrated on visible color variability and/or presence of lesions or other cosmetic anomalies. Leaf ratio (L/W) was determined by dividing representative leaf sample lengths by their width. Finally, head response (weather) was determined by observing the heads at maturity. These field observations focus on the presence or absence of bronzing, nectrotic or chlorotic lesions or any abiotic responses to environmental conditions.

BRIEF DESCRIPTION OF THE DRAWINGS

The accompanying color photographic illustrations show typical fruit and foliage characteristics of a specimen plant of 'PS-MSG0292', with colors being as true as possible with illustrations of this type.

The first drawing is a side elevational view of the fruit and foliage.

The second drawing is a close-up view of the fruit showing its physical dimensions.

The third drawing is close-up view showing a vertical cross-section of the fruit.

DETAILED BOTANICAL DESCRIPTION

The following observations, measurements, and values describe the new cultivar as grown in Chowchilla, Calif. The data was collected from first year tissue culture outplants. Selections were made in outdoor field settings. Plants are grown in the soil in rows. Row spacing (bed centers) is 38 inches, individual plant spacing varies between 12–36 inches, depending upon original seed germination. Stem segments were used to develop shoots which were transferred to a rooting medium for root development. These plants were then transplanted into the greenhouse for final plant growth and development. The date of first harvest is approximately May 15 and the date of final harvest is approximately June 10.

Color references are measured against The Munsell Book of Color, Munsell Color Macbeth Division of Kollmorgen Corporation.

Parentage: 'PS-MSG0292' was discovered and selected within the progeny of open-pollinated proprietary cultivar GGMSC6.

Classification: *Cynara scolymus L.* c.v. 'PS-MSG0292'.

Propagation: Asexual production either by tissue culture using stem segments to develop shoots for root development or division.

Plant:

*Height.*—Approximately 81.28–95.25 cm.

*Width.*—Approximately 165.10–200.66 cm.

*Form.*—Full.

*Growth habit.*—Upright.

*Plant vigor.*—10.0 cm (2–3 leaves)–95.25 cm (50–72 leaves) from fall planting (mid October) to final harvest (following May).

*Side shoots.*—Number: Approximately 3–7. Development: Heavy; some plants exhibit prominent, vigorous Development. Length: 68.0–103.0 cm, average 87.20. Diameter: 11.0 mm–20.0 mm, average 18.40 mm. Color: Color range: 2.5GY 9/2–2.5 GY 9/4; anthocyanin coloration present in basal portion, color range: 7.5R 6/4–7.5R 4/4.

*Main stem.*—Length: 18.5–26.3 cm, average 20.80 cm. Diameter: 41.0–32.0 mm, average 37.43 mm. Color: Highly pubescent, color range: 2.5GY 9/2–2.5GY 9/4; anthocyanin coloration at leaf insertion, color range: 7.5R 6/4–7.5R 5/4–7.5R 4/4. Leaves on main stem: Approximately 13–18, average 15.38 leaves.

*Foliage density.*—Dense; multiple, well-developed side-shoots increase density.

Capitulum:

*Size.*—Primary: Approximately 36.20–38.35 cm. Secondary: Approximately 33.78–35.56 cm.

*Shape.*—Oval to oval-spherical; predominantly oval-shaped.

*Number.*—Approximately 5–9 per plant.

*Texture.*—Slightly textured; some bracts exhibit uniform "blistered" appearance.

*Fragrance.*—Mild.

*Bract size.*—Length: Approximately 6.3–8.0 cm. Width: Approximately 5.1–6.1 cm.

*Bract shape.*—Predominantly oval-shaped; the basal region of some bracts is truncate.

*Bract texture.*—Slightly textured, some leaves exhibit uniform "blistered" appearance.

*Bract number.*—Approximately 57–62 per head.

*Bract color.*—Inner: 2.5 GY 9/2–5 GY 9/1. Outer: 2.5 GY 9/2.

*Bract firmness.*—Firm, thick, fleshy and well attached.

*Bract basal thickness.*—Approximately 5.0–7.0 mm.

*Heart description.*—Concave and full with a well developed shoulder.

*Heart color.*—10 Y 9/2–7.5 Y 9/2.

*Pappus length.*—Approximately 14.0–19.0 mm.

*Pappus color.*—Variable white but can vary slightly towards tan coloration, color range: 7.5Y 9/2–7.5Y 9/4.

*Overall cold storage response.*—Good; some regions that were damaged during harvest displayed some browning.

*Head firmness.*—Firm, head (capitula) are dense.

*Gloss.*—Dull, no sheen or glossiness visible.

*Cold storage* (*hold quality*).—Good, heads remain dense and free of decay.

*Head exterior* (*oxidation*).—Moderate; slight browning; some blackening on harvest damaged areas.

*Juiciness.*—Absent; no visible exudate observed.

*Head response* (*weather*).—No adverse responses to weather conditions were observed on heads (capitula) or other plant tissues.

*Bud burst.*—April 15–April 20.

*Bloom time.*—Approximately May 25–June 5.

*Duration of bloom.*—Approximately 37–40 days.

*Bloom diameter.*—7.62–12.70 cm; average 8.89 cm.

*Bloom depth.*—8.89–10.88 cm; average 9.94 cm.

*Bloom shape.*—Head.

*Florets.*—1021–1247 florets per head, average 1173 florets per head.

*Bud weight.*—Primary bud weight 455.3–472.4 grams, average 464.2 grams; secondary bud weight 420.7–450.3 grams, average 437.8 grams.

Foliage:

*Shape.*—Long strap-like leaves characterized by lobes that extend to the midvein, lobes are irregularly dentate.

*Length.*—Approximately 81.7–116.2 cm.

*Width.*—Approximately 39.2–67.2 cm.

*Leaf serrations.*—Approximately 1.5–5.6 cm.

*Leaf basal angle.*—Approximately 5–70 degrees.

*Leaf ratio* (*L/W*).—Approximately 1.24–2.63.

*Leaf area.*—Approximately 3243.49–7445.97 $cm^2$.

*Upper leaf surface color.*—Variable leaf coloration range: 2.5GY 4/4–2.5GY 3/4–5GY 4/6–5GY 4/4.

*Lower leaf surface color.*—Highly pubescent, color range: 5GY 7/2–5 GY 7/4–5GY 6/4.

*Texture.*—Slightly textured; most mature leaves have uniform "blistered" appearance.

*Venation.*—Intermediate and greenish; mid-vein is white to pale green, pubescence covers base color, color range 2.5GY 8/9–2.5GY 7/4–2.5GY 7/6; leaf lobe has greenish, less distinct appearance.

*Pubescence.*—Sparse; abundant on immature leaves but greatly reduced on mature leaves.

*Leaf basal thickness.*—Approximately 8.0–18.0 mm.

*Leaf distance between serrations.*—Approximately 2.9–4.7 cm.

*Petiole length.*—Approximately 4.0–10.0 cm.

*Petiole width.*—Approximately 2.8–4.7 cm.

*Petiole color.*—Pubescence covers base color; color range: 2.5GY 8/9–2.5GY 7/4–2.5GY 7/6; anthocyanin coloration extends from base of the petiole 60 mm, color range: 2.5R 5/4–2.5R 4/4.

Seeds:

*Shape.*—Compressed ovoid, can be angular, mid-section asymmetrical.

*Number.*—6–379 seeds per head; average 112 seeds per head.

*Length.*—8.0–9.0 mm; average 8.50 mm.

*Width.*—4.0–5.0 mm; average 4.29 mm.

*Color.*—Light brown, with tan hues in a speckled pattern.

Plant/bud disease resistance/susceptibility: Moderate infection of powdery mildew, *Leveillula taurica*, Ramularia spp. and Alternaria spp. leaf spot were noted; infection was observed throughout the plant's canopy.

General observations: 'PS-MSG0292' is male sterile lacking pollen on all florets during anthesis (flowering). 'PS-MSG0292' plants exhibit moderate height ranging from 81–95 cm. Compared to the head qualities of artichoke variety Green Globe, 'PS-MSG0292' has thicker fleshy bracts, thicker fleshy hearts (receptacles), oval shape and green (non-glossy) exterior coloration. These non-glossy heads (capitula) are large. 'PS-MSG0292' produces an average size (12) primary, size (18) secondary and size (24–36) tertiaries. Head numbers range between 5–9 heads per plant. Anthocyanin coloration is visible on both interior bracts and exterior lower bracts, color range 7.5R 6/4–7.5R 5/4–7.5R 4/4. The head spinosity is moderate with average spine length of approximately 1–2 mm. The plants upright growth habit is compact, but vigorous. The canopies' coloration is a medium green/yellow color ranging from lighter to darker shades. These colors range on the Munsell Leaf Color Chart 7.5 GY 4/8–7.5 GY 3/4and 7.5 GY 3/6–7.5 GY 3/4. Leaf spinosity is moderate, categorized as few. Floral stalk development during anthesis produces a purple flower, color range 10P 5/12–10P 4/12–10P 4/10–2.5P 3/10.

I claim:

1. A new and distinct cultivar of Artichoke plant named 'PS-MSG0292', as described and illustrated.

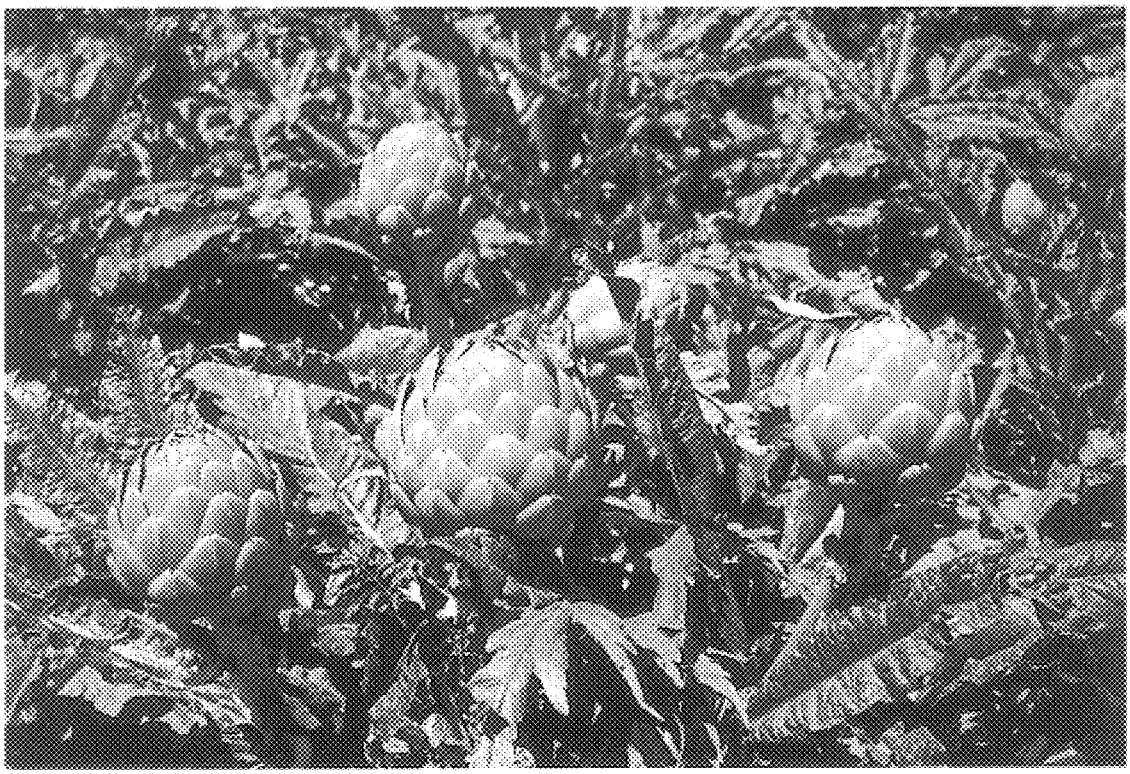

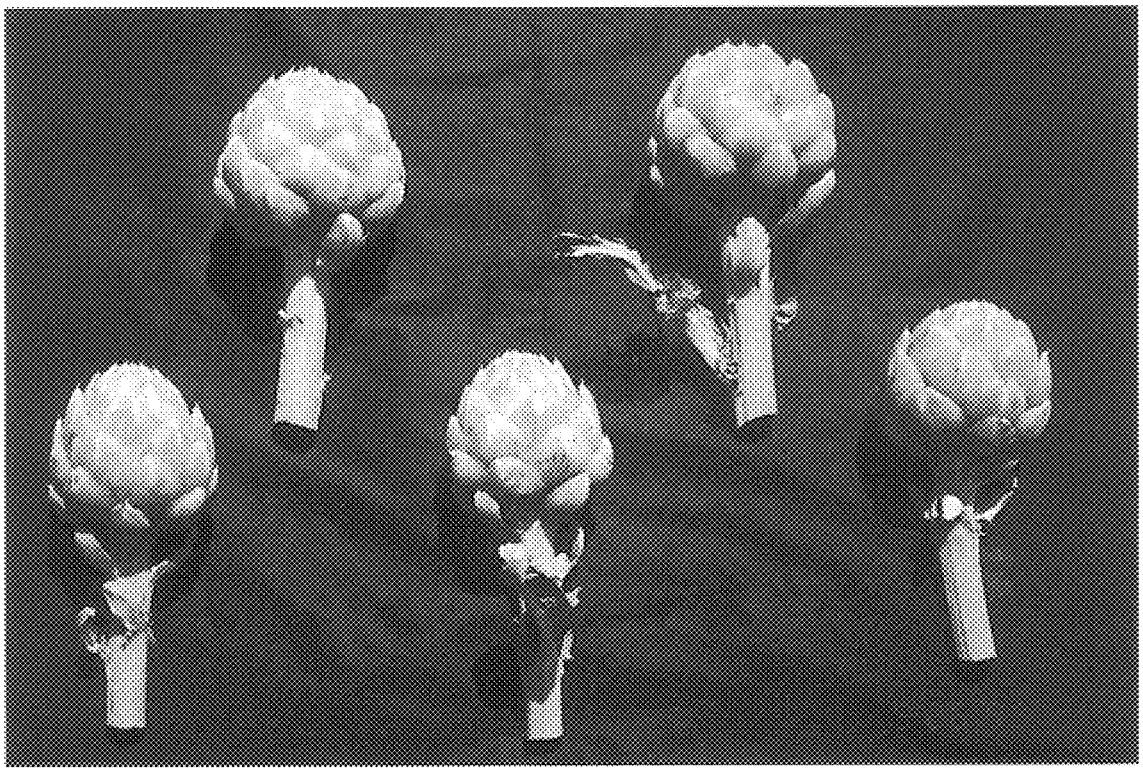

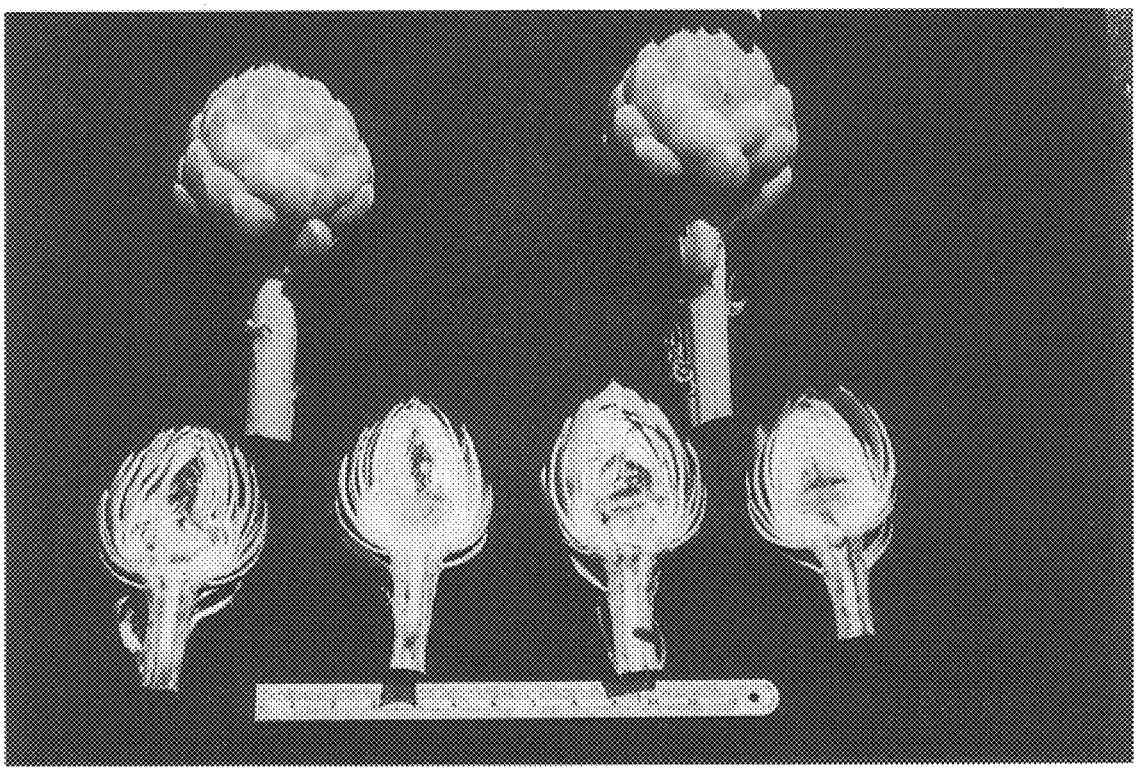

* * * * *